Figure 1:
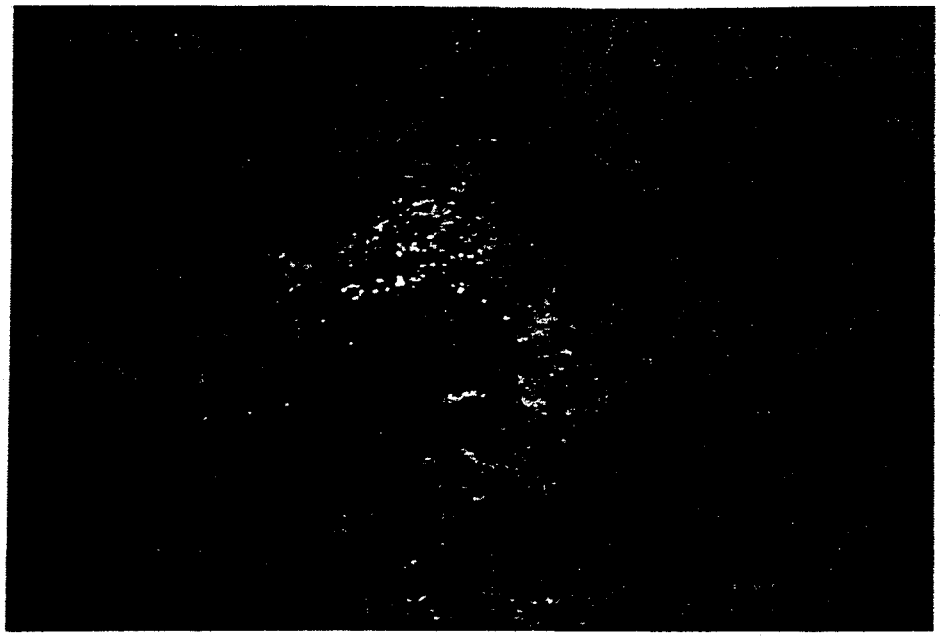

United States Patent [19]

Abdulla

[11] Patent Number: 5,104,657
[45] Date of Patent: Apr. 14, 1992

[54] COMBINATION PREPARATIONS CONTAINING CHLORAMPHENICOL, GENTAMICIN AND NYSTATIN AS ACTIVE INGREDIENTS FOR THE TOPICAL TREATMENT OF INFLAMMATORY SKIN DISORDERS

[76] Inventor: Souhail Abdulla, Rhauderwieke 1, D-2953 Rhauderfehn, Fed. Rep. of Germany

[21] Appl. No.: 620,763

[22] Filed: Dec. 3, 1990

[30] Foreign Application Priority Data

Dec. 14, 1989 [DE] Fed. Rep. of Germany ....... 3941263

[51] Int. Cl.$^5$ ...................... A61K 7/00; A61K 31/00; A61K 9/06; A61K 37/24
[52] U.S. Cl. ...................... 424/401; 514/31; 514/39; 514/179; 514/855; 514/861; 514/871; 514/887; 514/914; 514/731
[58] Field of Search ......................... 424/401

[56] References Cited

U.S. PATENT DOCUMENTS 4,882,167 11/1989 Jang ..................................... 424/469

*Primary Examiner*—Thurman K. Page
*Assistant Examiner*—Raj Bawa
*Attorney, Agent, or Firm*—Nixon & Vanderhye

[57] ABSTRACT

The invention relates to combination preparations containing chloramphenicol, gentamicin, nystatin and optionally a cortisone as active ingredients for the topical treatment of inflammatory skin disorders. The preparations are present preferably in the form of an ointment and have proved to be surprisingly effective particularly in the case of the treatment of skin disorders which are difficult to heal such as chronic eczema, inflammations in the anal and genital region, and of ulcus cruris and similar disorders.

7 Claims, 5 Drawing Sheets

COMBINATION PREPARATIONS CONTAINING CHLORAMPHENICOL, GENTAMICIN AND NYSTATIN AS ACTIVE INGREDIENTS FOR THE TOPICAL TREATMENT OF INFLAMMATORY SKIN DISORDERS

The invention relates to combination preparations for the topical treatment of inflammatory skin disorders, and in particular skin disorders which are difficult to heal such as chronic eczema, eczematous inflammations in the anal and genital region and secondary wounds and abscesses such as ulcus cruris, decubitus and furuncles.

The preparation according to the invention can, moreover, be used for the topical treatment of skin burns, intertrigo and impetigo and of chronic non-specific sores in the region of the corner of the mouth.

The above-mentioned skin disorders and secondary inflammations have already been treated hitherto with antibiotics of many different types and with cortisones. In many cases, however, a complete and permanent closure of the wounds cannot be achieved with conventional agents. This is true in particular of the various manifestations of ulcus cruris and in the case of proctological complaints such as eczemas and fissures in the anal region. Experience has shown that such wounds heal very poorly and the skin which is only superficially closed reopens quickly when stressed. Thus anal fissures for example can be remedied in severe cases only by surgery or by scab formation. Such a treatment can, however, lead to serious delayed consequences such as stenoses.

Surprisingly, it has become apparent according to the invention that by combining the per se known antibiotics chloramphenicol (I-Chla), gentamicin (II-Gt) and nystatin (III-Ns), a preparation for topical application is obtained which heals even extreme and stubborn skin disorders and secondary wounds permanently and in a relatively short time. Thus, complete healing was achieved in more than 80% of the cases particularly in the treatment of anal fissures in an advanced stage.

According to a preferred embodiment of the invention the preparation additionally comprises a cortisone (IV-Cort). Through the addition of such cortisone, as defined below, in very low amounts it is possible to enforce the therapeutic effect of the preparation of the invention (see example 7).

According to the invention, the indications chosen for the above-mentioned active ingredients include their structural analogues and derivatives having the same effect. In the case of chloramphenicol, the name can include, for example, its stereoisomers and the chloramphenicol-pantothenate complexes. In the case of gentamicin, gentamicin $C_1$, $C_2$ and $C_{1A}$ and the sulphates of these gentamicins are included according to the invention. The same applies to the various nystatins, for example nystatin $A_1$ and $A_2$ and for the cortisone derivatives, the term "cortisone" particularly including hydrocortisone and derivatives thereof.

The combination preparations according to the invention contain the active ingredients I-Chla, II-Gt and III-Ns in the weight ratio of (4 to 12) to (0.5 to 1.5) to (20 to 60), preferably (6 to 10) to (0.75 to 1.25) to (30 to 50) and in a particularly preferred manner (8) to (1) to (40), based in each case on the weight of the basis compound.

If IV-Cort is added, the active ingredients I-Chla, II-Gt, III-Ns and IV-Cort are present in the weight ratio of (4 to 12) to (0.5 to 1.5) to (20 to 60) to (1.5 to 4.5), preferably (6 to 10) to (0.75 to 1.25) to (30 to 50) to (2 to 4) and in a particularly preferred manner (8) to (1) to (40) to (3), based in each case on the weight of the basis compound.

According to a particularly preferred embodiment of the invention, the combination preparations are present in the form of ointments. To this end, the active ingredients can be incorporated in conventional ointment bases, and the latter should be chosen with regard for the indication provided for in each case.

For example, lipophilic bases composed of hydrocarbons or glyceride fats such as Vaseline or oils or mixtures thereof, which release the incorporated active ingredients slowly and can in this way exert a depot effect, come into consideration. A preparation of liquid paraffin and polyethylene obtainable commercially under the name Plastibase is particularly suitable.

Moreover, emulsifying fat bases (absorption bases) can be used which contain emulsifiers in addition to the fatty substances mentioned (Vaseline, paraffin, glyceride fats, waxes). They absorb water and aqueous solutions to form stable water-in-oil emulsions and are suitable for the preparation of water-free and water-containing ointments from which the combination of active ingredients is released at a consistent rate. Suitable emulsions can be prepared with emulsifier mixtures such as those present in, for example, wool wax.

Good absorption bases for the combination of active ingredients according to the invention are, for example, mixtures of paraffin, Vaseline, a fatty alcohol such as cetyl alcohol and wool wax or emulsions of Lazeran (wool wax alcohol ointment according to German Pharmacopoeia 9-FRG), liquid paraffin and Sorbol M (corresponding to Parben M), and Sorbol P (corresponding to Parben P). Other emulsifiers and emulsifier mixtures e.g. mono- and diglycerides of fatty acids or esters or ethers of various sugars with fatty acids or fatty alcohols can be used instead of wool wax or wool wax alcohols and derivatives. Thus, for example, a w/o emulsion of triglycerides of average chain length, liquid paraffin and white soft paraffin with the emulsifiers propylene glycol monostearate, glycerin monostearate, cetyl-stearyl alcohol, propylene glycol and polyethylene glycol-sorbitan derivatives, purified water and silicon dioxide in the highly disperse form have proved to be suitable.

One of the above-mentioned ointment bases, but without silicon dioxide, can be used for the preparation of an ointment compatible with eyes.

According to the invention, a neutral ointment basis in combination with at least approx. 20 to 30% by wt. ointment basis PL (Plastibase), based on the total mixture, has proved to be particularly suitable.

According to the invention, such ointments can contain 100 to 300 mg I-Chla, 10 to 35 mg II-Gt, 700 to 1100 mg III-Ns and optionally 60 to 100 mg IV-Cort per 100 g of total product.

According to a particularly preferred embodiment of the invention, such an ointment contains approx. 200 mg I-Chla, approx. 25 mg II-Gt, approx. 900 mg III-Ns and approx. 80 mg IV-Cort per 100 g of total product.

The combination preparations according to the invention can, moreover, be incorporated as lotions and in eye-compatible liquids for drops in a concentration of 0.8 to 1.5% by wt. whilst retaining the above-mentioned quantity ratios of the active ingredients to each other. For example, vegetable oils such as oleum neutralium and distilled water come into consideration as a liquid basis.

Surprisingly, it has become apparent according to the invention that, with preparations containing the above-mentioned active ingredients in combination, a therapeutic effect occurs of the kind that can not be achieved by means of the individual components or known combinations of the same as e.g. chloramphenicol/cortisone, gentamicin/cortisone and nystatin/cortisone with therapeutically acceptable doses. In this connection, a particular advantage of the preparations according to the invention lies in the fact that the gentamicin and optionally the cortisone components, which are problematic in terms of their side effects, are present in doses well below the critical limit but on the other hand a surprising therapeutic effect is achieved due to the combined effect of the constituents. Consequently, a true synergistic effect is involved during the treatment of inflammatory skin disorders which are otherwise difficult to treat. Surprisingly, no resistance was observed, even during long-term treatment.

The invention is explained below on the basis of examples.

EXAMPLE 1

Preparation of an Ointment Preparation

An ointment was prepared from the following constituents:
  chloramphenicol—200 mg
  gentamicin sulphate—25 mg
  nystatin—900 mg
  hydrocortisone—80 mg
  Ointment basis: Mixture of polyethylene and light liquid paraffin (Plastibase) (50 g) and Lazeran (ad 100 g).

The constituents were mixed homogeneously in the usual way to form an ointment.

EXAMPLE 2

A woman aged about 50 with ulcus cruris on the left side as a consequence of a post-thrombotic syndrome had been treated unsuccessfully for about 1½ years with conventional agents. The ulcer was approximately 2×3 cm in size and 0.5 cm deep (cf. FIG. 1).

Figure 2:

After the ointment according to the invention (see example 1) had been applied three times a day to the open place, a distinct improvement occurred after only one week's treatment (cf. FIG. 2).

Figure 3:

After a further 3½ weeks during which the ointment according to the invention was applied initially three times a day and subsequently twice a day, complete healing occurred. A stable layer of skin which was also capable of withstanding stresses such as knocks formed in the original region of the wound (cf. FIG. 3).

EXAMPLE 3

A boy now aged about 12 years who was reliant on a walking apparatus suffered from open pressure sores and abrasions which had been caused by the apparatus. With the conventional ointments including antibiotics or preparations containing cortisone it was not possible to heal permanently the places which repeatedly became inflamed.

After the ointment according to the invention (see example 1) had been applied, the wounds closed within about 4 to 7 days. As a result of prophylactic treatment 2 to 3 times a week of the places exposed to risk, the occurrence of renewed wounds could be avoided in a permanent manner. The prophylactic treatment was carried out over a period of 8 years. No resistance occurred during this period!

EXAMPLE 4

Figure 4:
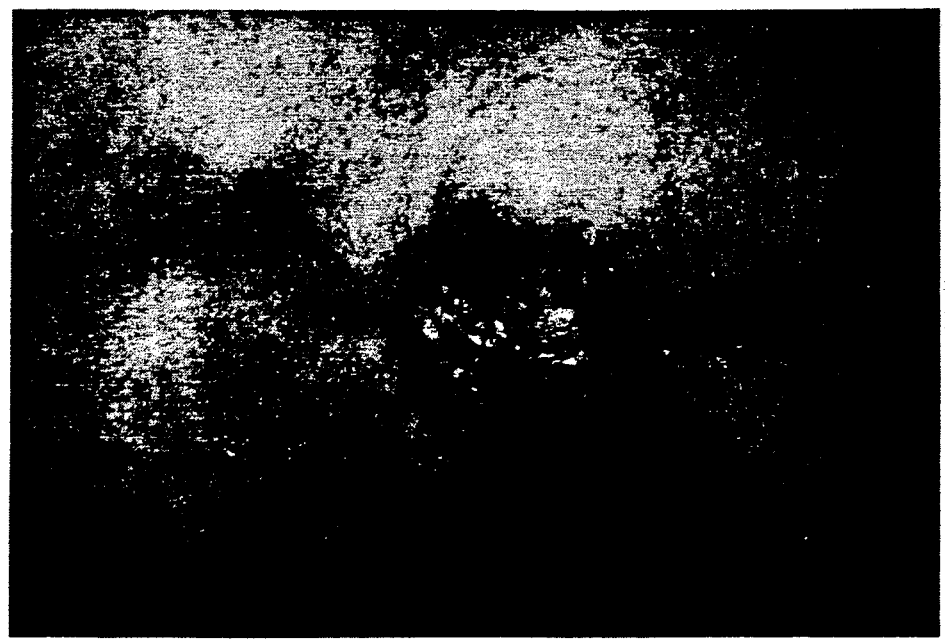

The same boy as described in Example 3 was born with spina bifida with a thoracolumbar meningomyelocoele the size of the palm of a hand. Due to the size of the myelocoele, an operation was out of the question. After about 3 months the myelocoele burst and a purulent liquid was discharged; against all expectations, the child survived the crisis. Initially, the wound was treated largely unsuccessfully with conventional ointments, including antibiotics and preparations containing cortisone. The combination preparation according to the invention (see example 1) was then used and the wound began to close after a few days. After 3 to 4 weeks the wound was completely covered with a fine skin which became increasingly strong during the weeks that followed. The wound has since closed (cf. FIG. 4).

EXAMPLE 5

A 33 year old man was severely wounded in Israel in an incendiary attack in February 1989 and lay unconscious for 3 months in hospital.

As a consequence of being confined to bed he acquired 3 decubitus sores of which one, an open wound about the size of a plum, was situated on the buttocks, a second sore with a diameter of about 8×10 cm was in the region of the right hip and a third sore with a diameter of about 7×9 cm was on the left hip.

The sores extended as far as the muscle. The sores were treated initially with erythromycin ointment, Refobacin ointment and Leukomycin ointment in an Israeli hospital. The treatment remained unsuccessful, however.

The attending physician then tried to treat the sores with a combination of Leukomycin and cortisone.

An attempt was then made in the same hospital to close the wounds with a combination of Refobacin and cortisone. After several weeks, however, this treatment too remained unsuccessful.

Finally, an attempt was made to treat the sores with home remedies such as sugar and salt solutions, disinfectants and even with honey.

In June 1989 the patient was transferred to Germany and lay in a hospital there for about 3 months. He had regained consciousness but the decubitus sores did not heal.

He was referred to a plastic surgery specialist and the latter recommended treating the sores by chiroplastic surgery. However, he admitted that the chance of success was only about 50%. The duration of the treatment was estimated at 6 months and the costs at about DM 100,000.-to 150,000.

For cost reasons, it was not possible to carry out this treatment.

The patient was subsequently taken in to be cared for by his brother.

When the inventor heard of this case, he offered his assistance.

Figure 5A:
Figure 5B:
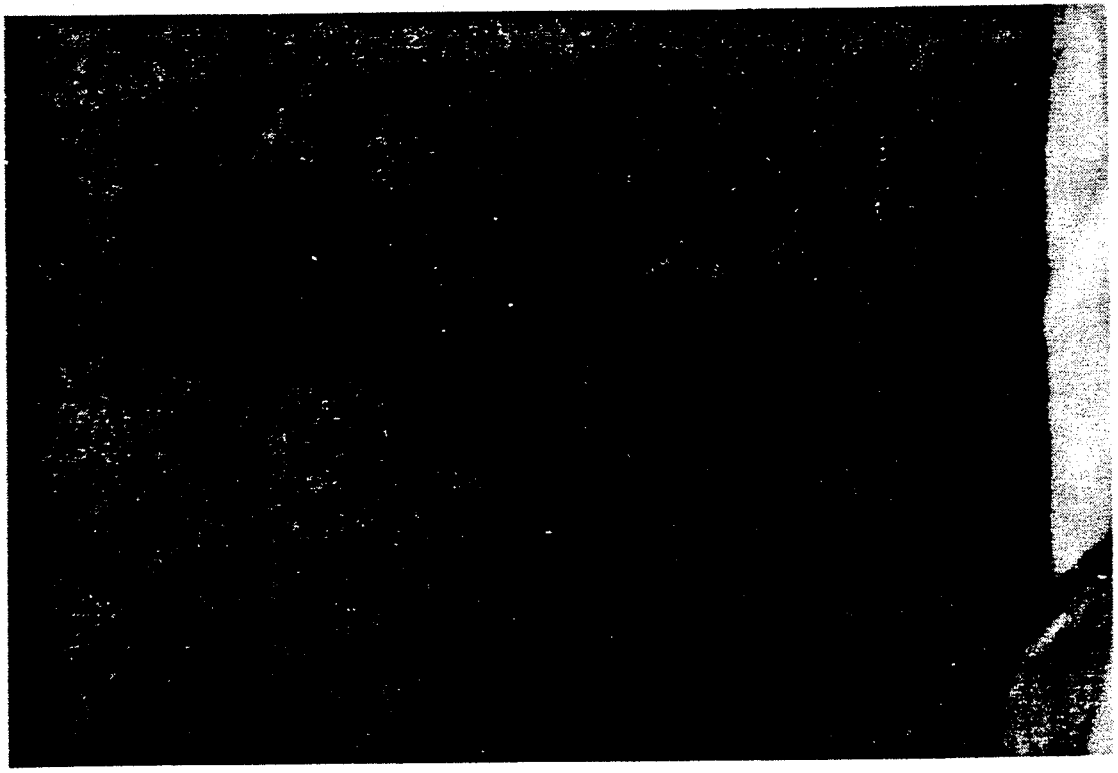

He began the treatment with the ointment according to the invention (see example 1) in October 1989. The wound on the buttocks closed without irritation after only 5 weeks. FIG. 5A is a photograph of the wound before the treatment and FIG. 5B is a photograph after 5 weeks' treatment.

Figure 6A:
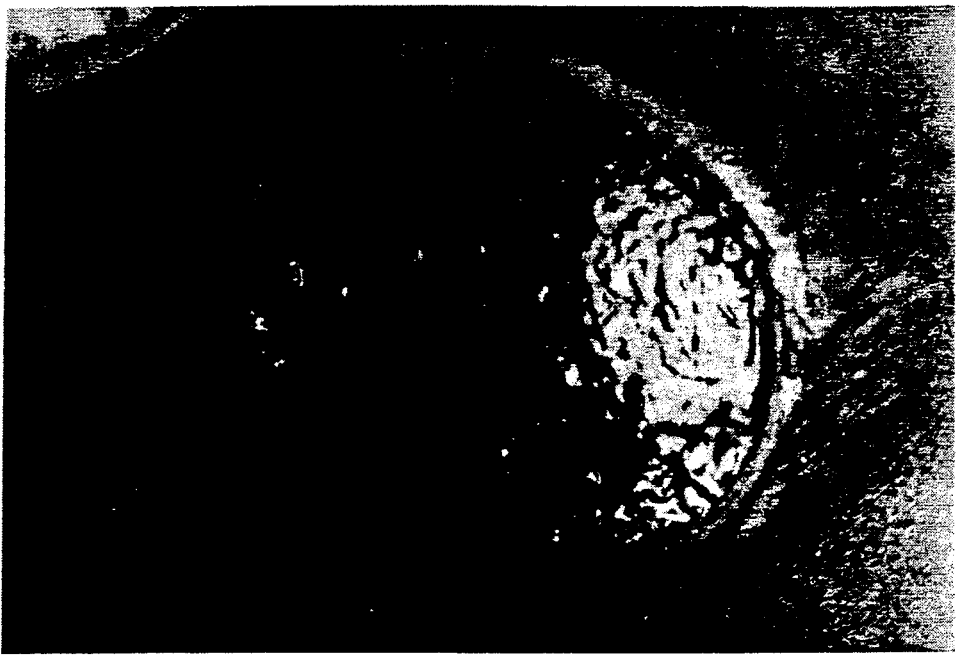
Figure 6B:
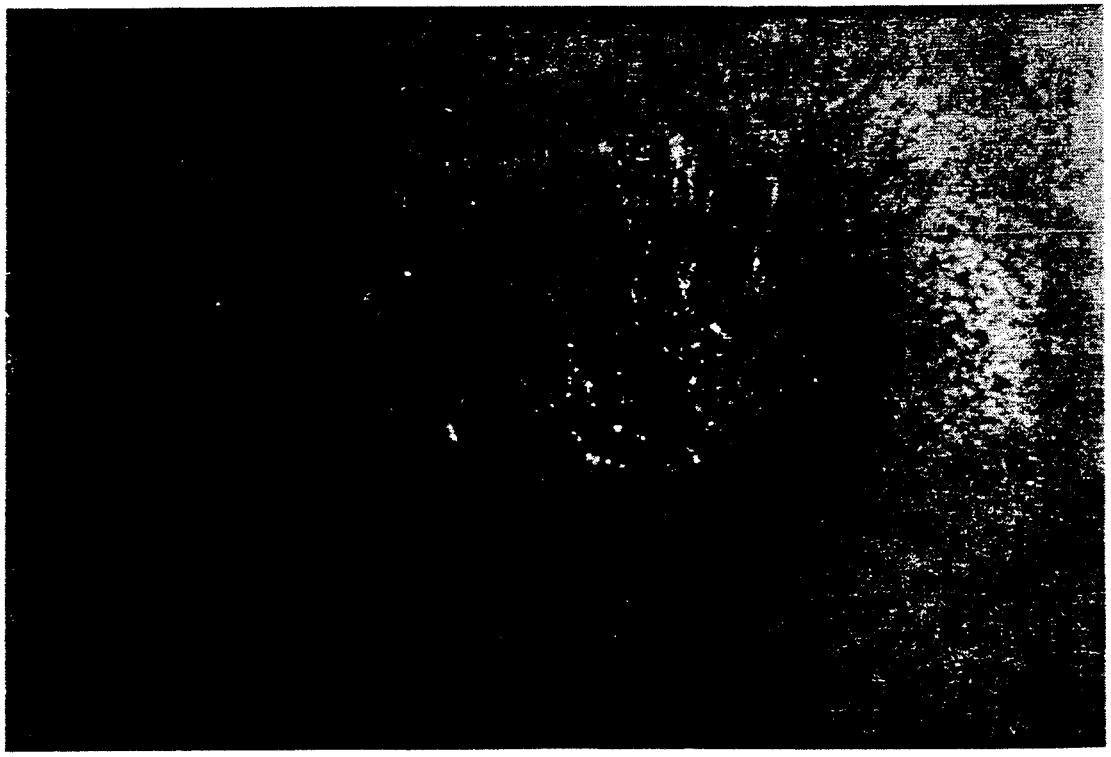

After 11 weeks the second wound on the right hip had almost completely closed except for a small trace. FIG. 6A is a photograph of the wound before the treatment and FIG. 6B is a photograph after 11 weeks' treatment.

Figure 7A:
Figure 7B:

After 11 weeks the third wound on the left hip was about 80% closed without irritation. FIG. 7A is a photograph of the wound before the treatment and FIG. 7B is a photograph after 11 weeks' treatment. In this condition the patient was flown back to Israel at the beginning of 1990. There the treatment with the ointment according to the invention was continued.

A short while later all the wounds had closed up completely.

EXAMPLE 6

Therapy Report on 237 Patients with Inflammation in the Anal Region

A. Patient structure

The total number of patients was 237. Of these, 112 were women and 125 were men. The ages ranged from 18 to 69 and the average age was about 39 years. 155 of the patients suffered from chronic anal eczema, 37 from chronic anal fissures and 45 from chronic anal eczema combined with anal fissures.

All the patients had previously been treated unsuccessfully several times with various proctological preparations that can normally be applied topically. Examples of the preparations already used are antibiotics, antimycotics, corticoid preparations and physical measures such as sitz baths.

169 of the patients had been treated 1 to several times with combination preparations such as chloramphenicol/cortisone, gentamicin/cortisone or nystatin/cortisone without clinical success.

B. Treatment specification

All the patients applied the ointment according to the invention twice a day. Patients with anal fissures applied the ointment according to the invention additionally after each bowel motion.

C. Results

1) In the case of the patients with anal eczema, the irritation disappeared after 2 to 10 days.

2) In the case of the patients with anal fissures, the discomfort during defecation disappeared after 3 to 14 days.

The patients were considered to be healed when they remained free from discomfort for at least 10 weeks after they had finished using the ointment. They were monitored at intervals of 1 to 2 weeks. On average, complete healing occurred after about 14 days.

The success rate is shown below in Table 1:

TABLE 1

|  | No. of patients | Healed | Improved |
| --- | --- | --- | --- |
| Chronic anal eczema | 155 = 100% | 138 = 89% | 17 = 11% |
| Chronic anal fissures | 37 = 100% | 31 = 84% | 4 = 16% |
| Chronic anal eczema with anal fissures | 45 = 100% | 36 = 80% | 9 = 20% |

The results show that the combination preparation according to the invention surprisingly developed an excellent effect with a healing rate of 80 to 89% during the treatment of anal eczema and anal fissures or combinations thereof.

It should be pointed out in this connection that the individual active ingredients are present in a very low dose in each case but in combination exhibit an extremely high and hitherto unobserved degree of efficacy. According to the clinical observations, this effect can be explained only by a synergistic effect.

D. Side effects

Only in 33 of the patients treated (15.6%) did slight stinging lasting for about 5 to 15 minutes occur at the beginning of the treatment after application of the ointment. The stinging ceased, however, after a few days' application. No other side effects or allergies were observed.

EXAMPLE 7

A group of 20 patients suffering from chronic anal eczema, the group having a structure similar to Example 6 was treated as described in Example 6 with the difference that the preparation of the invention as used did not contain hydrocortisone.

The therapeutic effects described in Example 6 were confirmed; it was however observed that at average the irritation disappeared 1 to 2 days later and actual healing was obtained 2 to 4 days later than described in the previous example.

The results demonstrate that the surprising therapeutic effect is obtained by the combination of chloramphenicol, gentamicin and nystatin, and that this effect is expedited to an unexpected degree by very low amounts of cortisone.

I claim:

1. A topical composition for the treatment of inflammatory skin disorders consisting essentially of chloramphenicol, gentamicin and nystatin in a weight ratio of 4–12:0.5–1.5:20–60, respectively in a topically acceptable carrier.

2. The topical composition of claim 1 further including cortisone in a weight ration of 1.5–4.5.

3. The topical composition of claim 1 wherein the carrier is an ointment base.

4. The topical composition for the treatment of inflammatory skin disorders consisting essentially of 100–300 mg chloramphenicol 10–35 mg gentamicin, and 700–1,100 mg nystatin per 100 g of topically acceptable carrier.

5. The topical composition of claim 4, further including 60 to 100 mg of cortisone per 100 g of carrier.

6. A method of treating inflammatory disorders of the skin and mucus membranes topically applying to the affected, inflamed area an effective amount of a composition consisting essentially of chloramphenicol, gentamicin and nystatin in a weight ratio of 4–12:0.5–1.5:20–60, respectively in a topically acceptable carrier.

7. The method of claim 6 wherein the composition also includes cortisone in a weight ratio of 1.5–4.5.

* * * * *